US006387073B1

(12) United States Patent
Weiler et al.

(10) Patent No.: US 6,387,073 B1
(45) Date of Patent: May 14, 2002

(54) HERMETICALLY SEALED CONTAINER WITH MEDICAMENT STORING AND DISPENSING INSERT

(75) Inventors: Gerhard H. Weiler, Woodstock; Frank N. Leo, Crystal Lake, both of IL (US)

(73) Assignees: Weiler Engineering, Inc., Elgin; Automatic Liquid Packaging, Inc., Woodstock, both of IL (US)

( * ) Notice: Subject to any disclaimer, the term of this patent is extended or adjusted under 35 U.S.C. 154(b) by 0 days.

(21) Appl. No.: 09/731,128

(22) Filed: Dec. 6, 2000

(51) Int. Cl.[7] .............................................. A61M 3/100
(52) U.S. Cl. ......................................... 604/87; 206/222
(58) Field of Search ........................... 222/81, 83, 129; 206/219, 221, 222; 215/DIG. 8; 604/82–92

(56) References Cited

U.S. PATENT DOCUMENTS

| | | | | |
|---|---|---|---|---|
| 2,721,552 A | | 10/1955 | Nosik | 128/272 |
| 2,773,591 A | | 12/1956 | Jensen | 206/47 |
| 3,731,853 A | | 5/1973 | Baumann et al. | 222/386 |
| 3,739,947 A | | 6/1973 | Baumann et al. | 222/136 |
| 3,762,542 A | | 10/1973 | Grimes | 206/58 |
| 3,796,303 A | * | 3/1974 | Allet-Coche | 604/82 |
| 3,924,741 A | * | 12/1975 | Kachur et al. | 604/82 |
| 4,136,775 A | | 1/1979 | Zaltsman | 206/219 |
| 4,386,696 A | | 6/1983 | Goncalves | 206/221 |
| 4,596,110 A | | 6/1986 | Weiler | 53/410 |
| 4,638,927 A | | 1/1987 | Morane | 222/83 |
| 4,707,966 A | | 11/1987 | Weiler et al. | 53/410 |
| 4,903,865 A | | 2/1990 | Janowitz | 222/83.5 |
| 4,982,875 A | * | 1/1991 | Pozzi et al. | 604/87 |
| 5,409,141 A | | 4/1995 | Kikuchi et al. | 222/81 |
| 5,772,017 A | | 6/1998 | Kang | 206/222 |
| 5,799,775 A | | 9/1998 | Spring | 206/222 |
| 5,927,549 A | * | 7/1999 | Wood | 222/83 |
| 5,944,175 A | * | 8/1999 | Albisetti | 206/219 |
| 5,950,819 A | | 9/1999 | Sellars | 206/221 |
| 5,971,140 A | * | 10/1999 | Frutin | 206/219 |
| 6,003,728 A | * | 12/1999 | Elliott | 222/129 |
| 6,138,821 A | * | 10/2000 | Hsu | 215/DIG. 8 |
| 6,148,996 A | * | 11/2000 | Morini | 215/DIG. 8 |
| 6,152,296 A | * | 11/2000 | Shih | 215/DIG. 8 |
| 6,230,884 B1 | * | 5/2001 | Coory | 215/DIG. 8 |
| 6,244,433 B1 | * | 6/2001 | Vieu | 206/221 |
| 6,247,586 B1 | * | 6/2001 | Herzog et al. | 206/221 |

* cited by examiner

*Primary Examiner*—Philippe Derakshani
*Assistant Examiner*—Thach H Bui
(74) *Attorney, Agent, or Firm*—Olson & Hierl, Ltd.

(57) ABSTRACT

A hermetically sealed container and a medicament bearing insert assembly therefor are disclosed. The medicament bearing insert assembly is protected by a severable overcap. A pocket within the insert assembly is provided with a pierceable membrane. Rupture of the membrane by a built-in plunger causes the medicament to drop out of the pocket and into the container where it is mixed with the container contents.

8 Claims, 5 Drawing Sheets

HERMETICALLY SEALED CONTAINER WITH MEDICAMENT STORING AND DISPENSING INSERT

FIELD OF THE INVENTION

This invention relates to a hermetically sealed container which includes a body filled with a liquid and, more particularly, to an insert for such a container adapted to store and thereafter dispense a medicament such as a tablet into the liquid in the container.

BACKGROUND OF THE INVENTION

Hermetically sealed containers can be readily produced by the so-called blow/fill/seal techniques. Utilizing such techniques, a container body is first blow molded from an extruded parison segment, then charged (or filled) with a desired liquid, and thereafter sealed with a preformed closure insert. See, for example, the container structure disclosed in U.S. Pat. No. 4,596,110 to Weiler.

The liquid in the container body is typically dispensed through the insert and then mixed with another liquid or solid deposit prior to being ingested or otherwise used. A disadvantage associated with the mixing of a deposit or the like into the liquid dispensed from the container prior to ingestion or use is the increased risk of contamination inherent in the handling, manipulation and mixing of the deposit such as a tablet or the like in a non-sterile environment.

There is thus presently a need for a hermetically sealed container where the liquid or solid deposit intended to be mixed with the liquid in the container is stored in the container and mixed with the liquid in the container prior to being dispensed From the container to eliminate the risk of contamination and to simplify the mixing and dispensing procedure.

SUMMARY OF THE INVENTION

A hermetically sealed container of the present invention incorporates a preformed medicament bearing insert assembly adapted and structured to store and thereafter dispense a solid medicament, such as a medicinal tablet or the like, into a liquid contained in the body of the container.

More particularly, the insert assembly defines a base member with sealed cavity having a rupturable unitary membrane therewith and a solid medicament contained in the cavity. A plunger provided in the insert assembly is adapted to penetrate the membrane so that the medicament can drop into the body of the container when the plunger is activated. The plunger can be axially slidable or threaded, as desired. The membrane is not completely severed from the base member, however, to dispense the medicament.

The medicament can be a tablet, a capsule, a pill, an aliquot of a powder, and the like.

The insert assembly is encapsulated within a hermetically sealed container molded of a thermoplastic material and having a body portion, a neck portion, and an severable overcap unitary therewith. The neck portion defines a socket for the insert assembly. The severable overcap is delineated from the neck portion by a peripheral frangible web, and protects the insert assembly during storage and handling from premature activation. When the overcap is removed or severed from the container by a twisting action, the plunger, which is part of the insert assembly, can be activated to release the medicament into the body of the container by urging the plunger against the membrane so as to partially sever the membrane from the insert assembly.

Other advantages and features of the present invention will be more readily apparent from the following detailed description of the preferred embodiment of the invent ion, the accompanying drawings, and the appended claims.

DETAILED DESCRIPTION OF THE PREFERRED EMBODIMENTS

Figure 1:
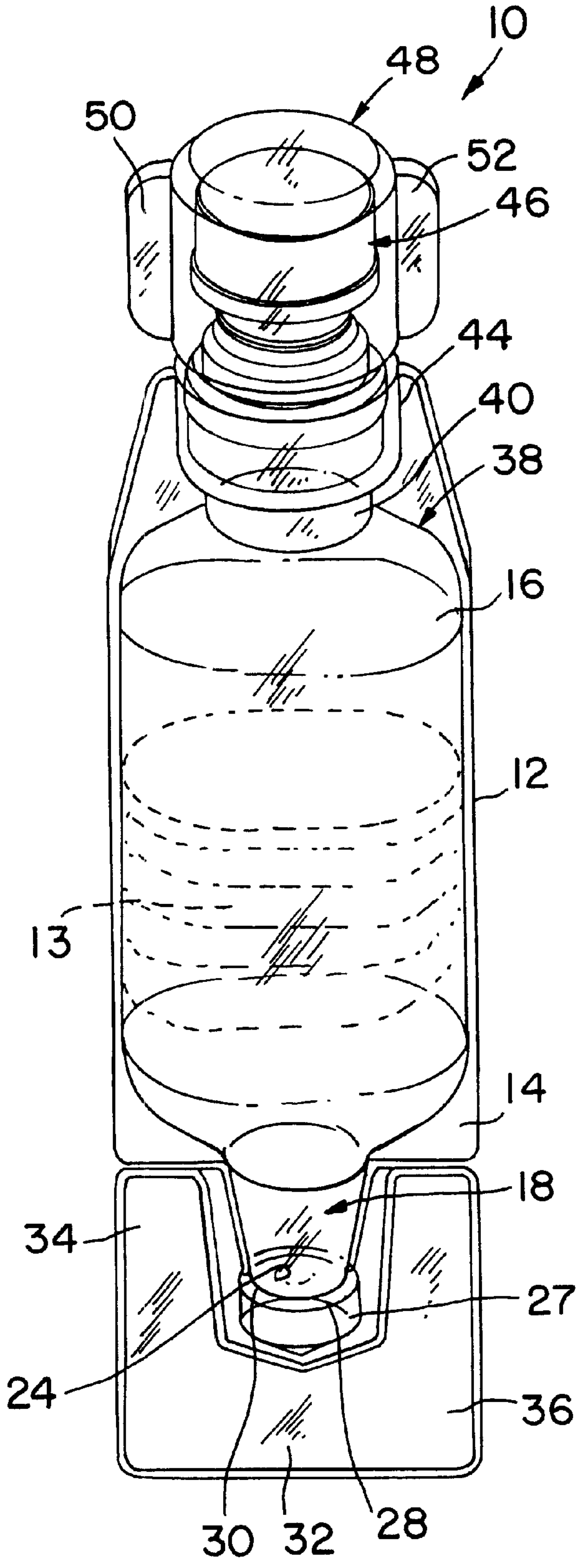
FIG. 1 is a perspective view of a hermetically sealed container embodying the present invention.

The invention disclosed herein is, of course, susceptible of embodiment in many different forms. Shown in the drawings and described below in detail are preferred embodiments of the container of the present invention. It is to be understood, however, that the present disclosure is an exemplification of the principles of the invention and does not limit the invention to the illustrate embodiments.

For ease o description, the container of the present invention will be described in a normal (upright) operating position and terms such as upper, lower, horizontal, etc., %ill be used with reference to this position. It will be understood, however, that the container and the insert assembly of the present invention may be manufactured, stored, transported, used, and sold in an orientation other than the position described.

A formed, filled, and hermetically sealed thermoplastic container 10 embodying the insert assembly structure of the present invention is illustrated in FIG. 1. Container 10 is preferably fabricated, using a method similar to the method disclosed in U.S. Pat. No. 4,596,110 to Weiler, from conventional molding materials such as polyethylene, polypropylene, and the like, compatible with the contemplated container contents.

Container 10 is but one example of such a container, inasmuch as a wide variety of contain r shapes and sizes can be fabricated. Container 10 includes a hollow body portion

12 having a bottom portion 14 and a top portion 16. The container body portion 12 is filled with a suitable liquid contents or solution 13. A medicament containing insert assembly 46 is received in a socket 44 provided in a neck portion 38 of the container 10. A severable overcap 48 envelops the upper part of insert assembly 46. The bottom portion 14 of the container 10 terminates in a dispensing nozzle 18 which is in fluid flow communication with the container body portion 12 and the liquid contents 13 therein.

Figure 3:
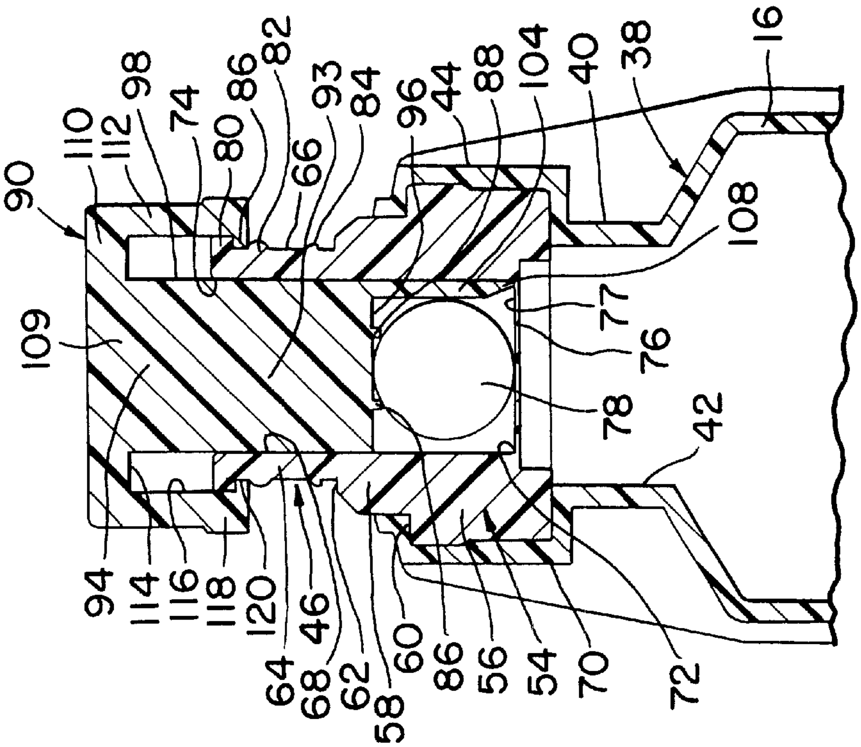
FIG. 3 is a cross-sectional view of the container socket and insert.
Figure 2:
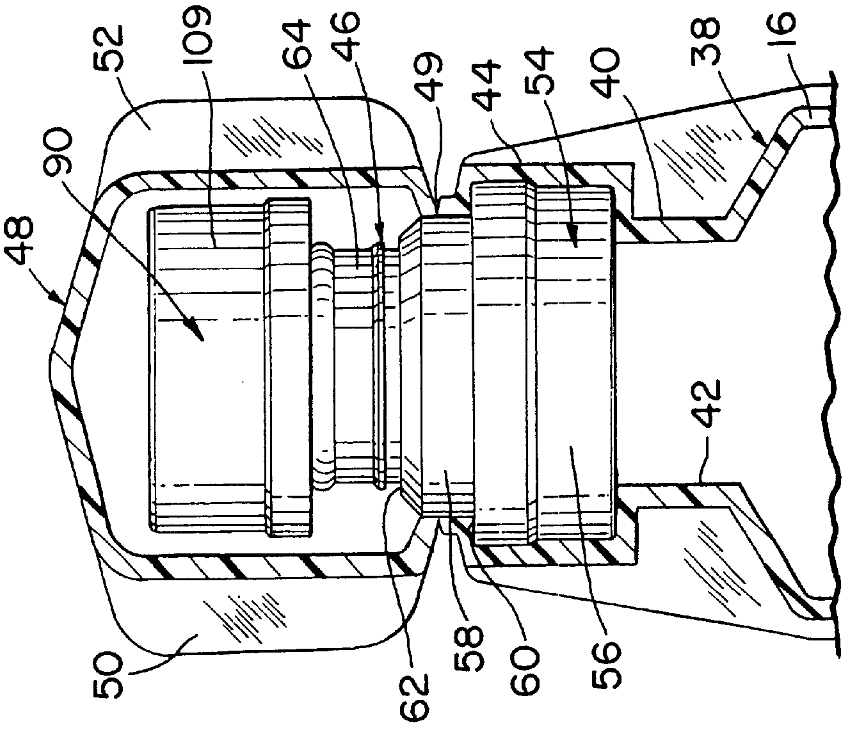
FIG. 2 is an enlarged, partial front elevational view, partially broken away and shows the insert received in a socket provided in the neck portion of the container.

As shown FIGS. 1, 2 and 3, at the top portion 16, the container body portion 1 terminates in the neck portion 38 unitary therewith which includes a general cylindrical throat portion 40 defining a hollow passageway 42. Socket 4A is defined by throat portion 40 and is unitary therewith. Socket 44 is sized to receive the insert assembly 46. Severable overcap 48 envelops insert assembly 46 and is delineated from the socket 44 by a frangible web 49. Preferably, overcap 48 includes two spaced apart unitary and diametrically opposed grasping wings 50 and 52 to facilitate removal of the overcap 48 when the container 10 is prepared for use.

Insert assembly 46 is a separately fabricated assembly adapted to be inserted, immobilized and subsequently sealed within the socket 44 of the container 10 using a top insertion method disclosed in, for example, U.S. Pat. No. 4,596,110 to Weiler and U.S. Pat. No. 4,707,966 to Weiler et al. The insert assembly 46 may be made of the same type of material as the container 10, i.e., polyethylene or polypropylene, but can also be molded from a different material such as acrylonitrile-butadiene-styrene (ABS), and the like.

Referring t FIGS. 2 and 3, the insert assembly 46 includes a base member 54 which is immobilized and sealed in the socket 44 of the container 10. The base member 54 defines a medicament pocket 70 and includes first and second collars 56 and 58, first and second shoulders 60 and 62 and a hollow neck 64. The shoulder 60 extends between the collars 56 and 58 while the shoulder 62 extends between the collar 58 and the neck 64. The base member 54 includes an outer surface 66 and defines a generally cylindrical inner passageway 68 which extends through the collars 56 and 58 and the neck 64 and defines the pocket 70 which terminates in a proximal generally circular aperture 72 occluded by rupturable membrane 76.

Interior face 77 of rupturable membrane 76 seals the interior of the pocket 70 from the container 10. The rupturable membrane 76 is unitary with and is made of the same material as the base member 54. The thickness of the material forming the membrane 76 is selected to provide both good sealing and piercing characteristics.

Medicament it 78 is stored in the pocket 70 and is sealed from the container body 12 by the membrane 76. Medicament 78 can be, for example, a capsule, a tablet, a pill, or an aliquot of powder, as desired.

The neck 64 of the base member 54 additionally includes a distal flange 80 extending radially outwardly from the outer surface 66 adjacent the distal opening 74. The neck 64 also includes first and second annular ribs 82 and 84 extending outwardly from, and circumferentially around, the outer surface 66. The rib 82 is positioned parallel to, and spaced from, the flange 80 so as to define a groove 86 therebetween. The rib 84 is positioned parallel to, and spaced from, the shoulder 62 so as to defme a groove or pocket 88 therebetween.

The insert assembly 46 also includes a plunger 90 movably received in passageway 68 defined in base member 54. Plunger 90 includes a generally cylindrically shaped head unitary with body portion 93 which extends into the passageway 68 o the member 54. The proximal end 94 of plunger 90 has a distal radial end face 96 and an outer surface 98 which abuts and slides against the inner surface of the base member 54 that defines the passageway 68.

The solid medicament 78 is stored in the pocket 70 so that it is retained between the end face 96 of the plunger 90 and the membrane 76. The radial end face 96 also c,n include a pair of spaced-apart prongs 86 and 88 extending outwardly therefrom which defme a cradle for the medicament 78. An elongate piercing blade 104 extends from the radial end face 96 outwardly toward the membrane 76 Outer face 106 of blade 104 slides along passageway 68 of the base member 5. The blade 104 terminates in a pointed tip 108 which is adapted to pierce and partially sever the membrane 76 when the plunger 90 is urged against the membrane 76.

Cap 109 o plunger 90 is unitary with the proximal end 94 of plunger body portion 93 d comprises an annular flange 110 which extends radially outwardly from t e outer surface 98 of the plunger body portion 93 adjacent the proximal end 94 thereof. A circumferential wall 112 depends generally downwardly from the flange 110. The wall 112 is spaced from and generally parallel to the cuter surface 98 of the plunger body portion 93 and defines a circumferential hollow sleeve 114 between the wall 112 and the outer surface 98. Annular flan ye 110 provides a stop as the plunger 90 is urged against the membrane 76. The membrane 76 is not fully severed from the base member 54 when medicament 78 is dispensed so as to keep the membrane 76 from dropping into the container 10 along with the medicament 78.

The wall 112 includes an inner surface 116 and a peripheral distal end 118. A finger 120 e tends circumferentially and radially inwardly from the inner surface 116 adjacent the peripheral distal end 118 thereof and abuts retaining rib 82.

Figure 9:
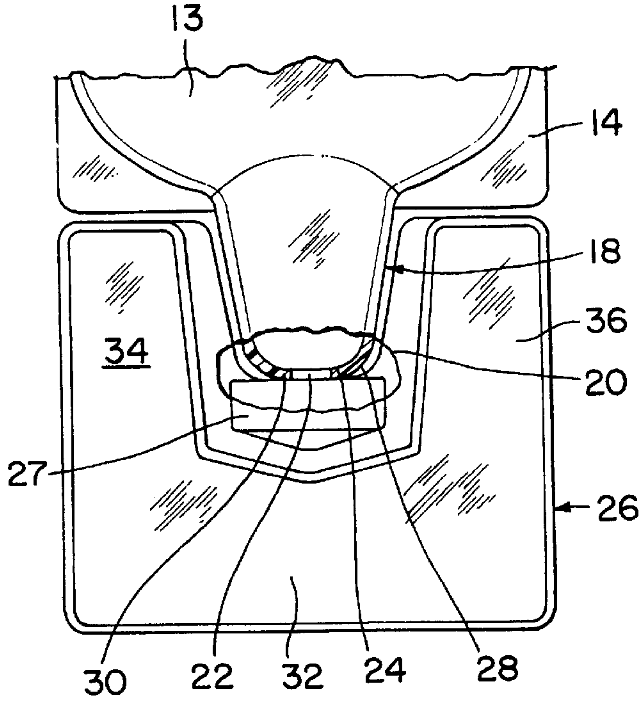
FIG. 9 is an enlarged partial front elevational view, partially broken away, and showing the dispensing nozzle of the container.
Figure 10:
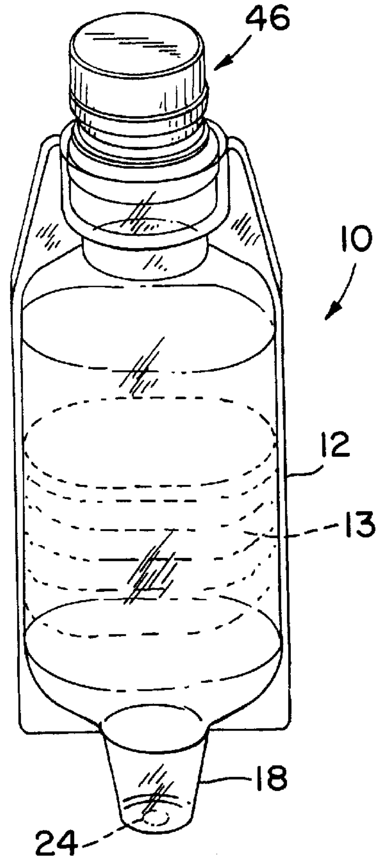
FIG. 10 is a perspective view depicting the container of FIG. 1 in its dispensing position with the overcap and dispensing cap removed therefrom and the medicament in the liquid dissolved in the contents of the container.

As shown n FIGS. 1, 9 and 10, the nozzle 18 at the bottom of container 10 is hollow, generally frustoconical in shape, and at distal end 20 defines an axial dispensing aperture 22. A unitary but removable dispensing cap member 26 is attached to the bottom distal end 20 of the nozzle 18. Dispensing member 26 includes a generally cylindrically shaped twist-off cap 27 including a circumferential lip or edge 28 which is unitary with the lip 24 of the nozzle 18. The lip 24 is delineated from the lip 28 by a circumferential frangible web 30 unitary therewith.

Dispensing member 26 additionally includes a flat lower base 32 which is unitary with the cap 27 and wings 34 and 36 extending upwardly from opposite ends of the base 32 and on opposite sides of the nozzle 18 in a diametrically opposed relationship.

The use and operation of the container 10 and the insert assembly 46 thereof for storing, dispensing and thereafter mixing the medication 78 with a liquid 13 in the container body 12 will now be described with reference to FIGS. 2–5, 9 and 10.

Initially, the overcap 48 is severed and removed from the container 10 to obtain access to the insert assembly 46 and the plunger 90 thereof. This is achieve by grasping the wings 50 and 52 of the overcap 48 and then exerting a substantially simultaneous twisting and lifting motion to the overcap 48 so as to break the unitary frangible web 49 (FIG. 2) between overcap 48 and container top portion 16.

FIG. 3 shows the container 10 with the overcap 48 removed therefrom. The plunger 90 of the insert assembly 46 is in its normal upright locked position where the finger 120 on the cap 109 of the plunger 90 is lodged in the pocket 86 defined n the neck 64 of the member 54 between flange 80 and retaining rib 82.

Figure 4:
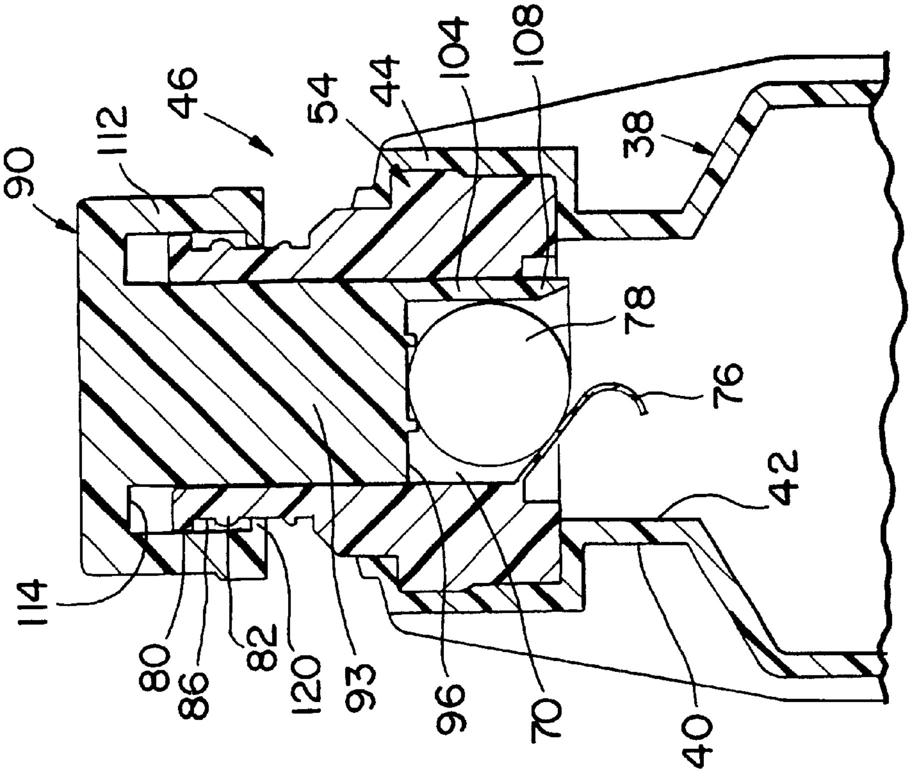
FIG. 4 is a cross-sectional view of the container socket and insert structure where the plunger of the insert assembly has pierced the membrane thereof preparatory to medicament release.

FIG. 4 depicts the top of the container 10 and the insert assembly 46 after the plunger 90 has been partially depressed downwardly in the direction of the base member 54. The finger 120 has been dislodged from the pocket 86 and has passed over the rib 82 on the neck 64 into a position where the finger 120 is located between the ribs 82 and 84 on the neck 64. The depression of the plunger 90 also causes the downward movement of the elongate blade 104 extending outwardly from the end of the head 92 which, in turn, causes the tip 108 thereof to contact and pierce the membrane 76.

Figure 5:
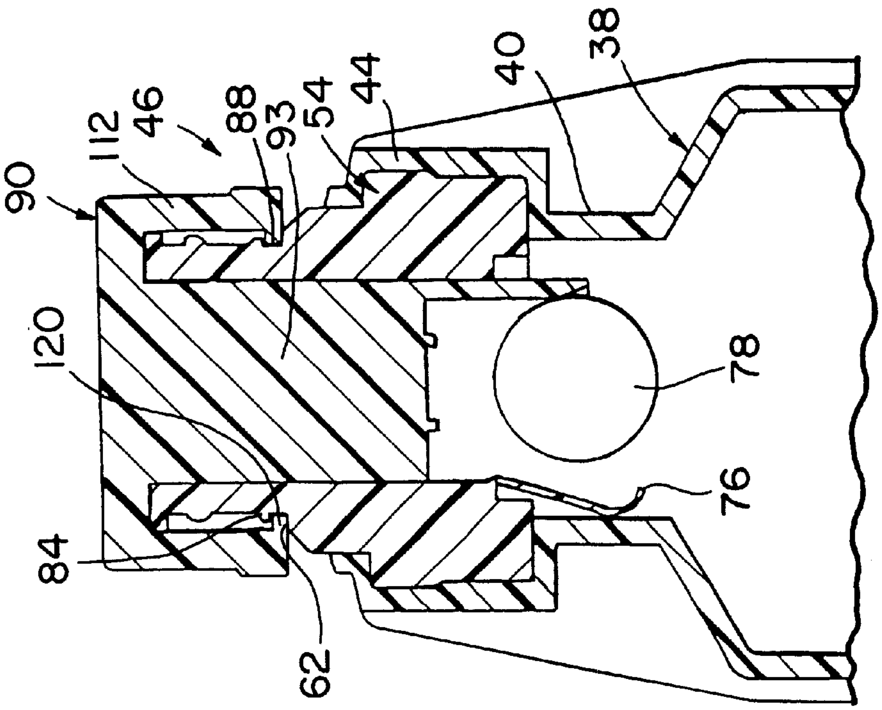
FIG. 5 is a cross-sectional view of the container socket and insert assembly depicting the plunger in a position where the medicament is released from the insert assembly into the body of the container.

The continued downward axial movement of the plunger 90 in the direction of the base member 54 into the position of FIG. 5 where the finger 120 of the plunger 90 is lodged in the pocket 88 on the neck 64 of the base member 54 causes the further downward movement of the plunger body portion 93 through the pocket 70 which, in turn, causes the medicament 78 to be pushed out of the pocket 70 through the now open aperture 72 in the base member 54 and into the container body 12 where the medicament 78 is dissolved and mixed in the liquid 13. The pierced membrane remains with the base member 54, however.

The container 10 at this point can be shaken to allow the composition of the medicament 78 to be thoroughly distributed in the liquid 11. The container 10 then can be turned upside down into a position where the dispensing nozzle 18 faces up and the dispensing member 26 is severed and removed from the nozzle 18 by grasping the wings 34 and 36 thereof and then exerting a simultaneous twisting and lifting motion to break the frangible web 30. The container 10 is then returned to the dispensing position of FIG. 7 for dispensing the liquid mixture.

Figure 7:
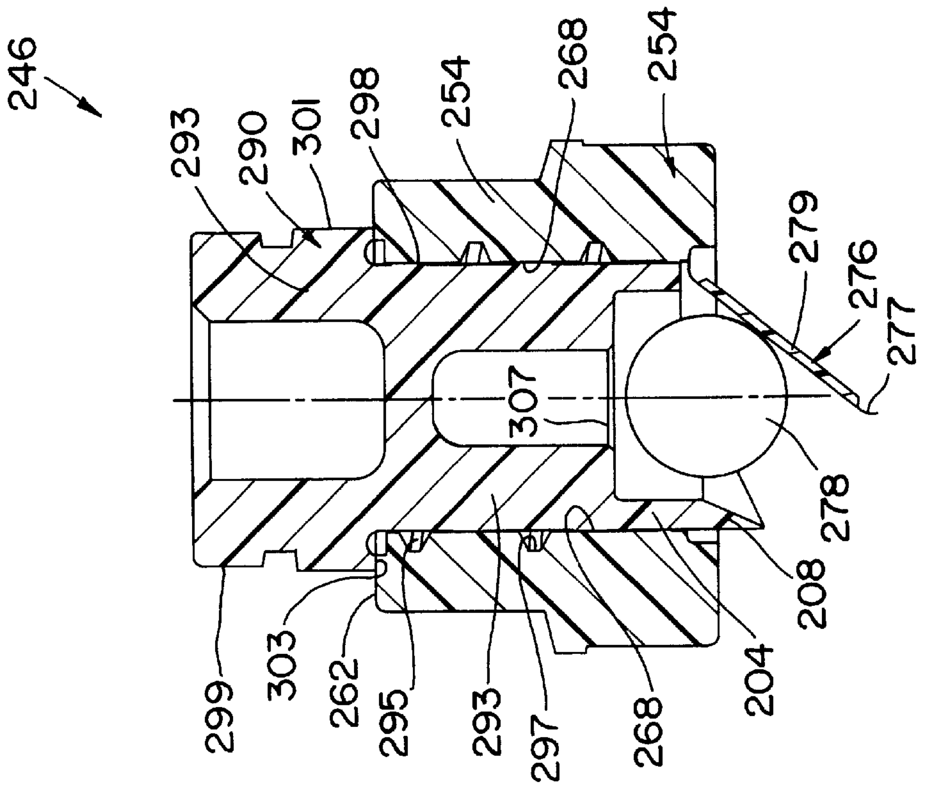
FIG. 7 is a view similar to FIG. 6 and showing a medicament being dispensed.
Figure 6:
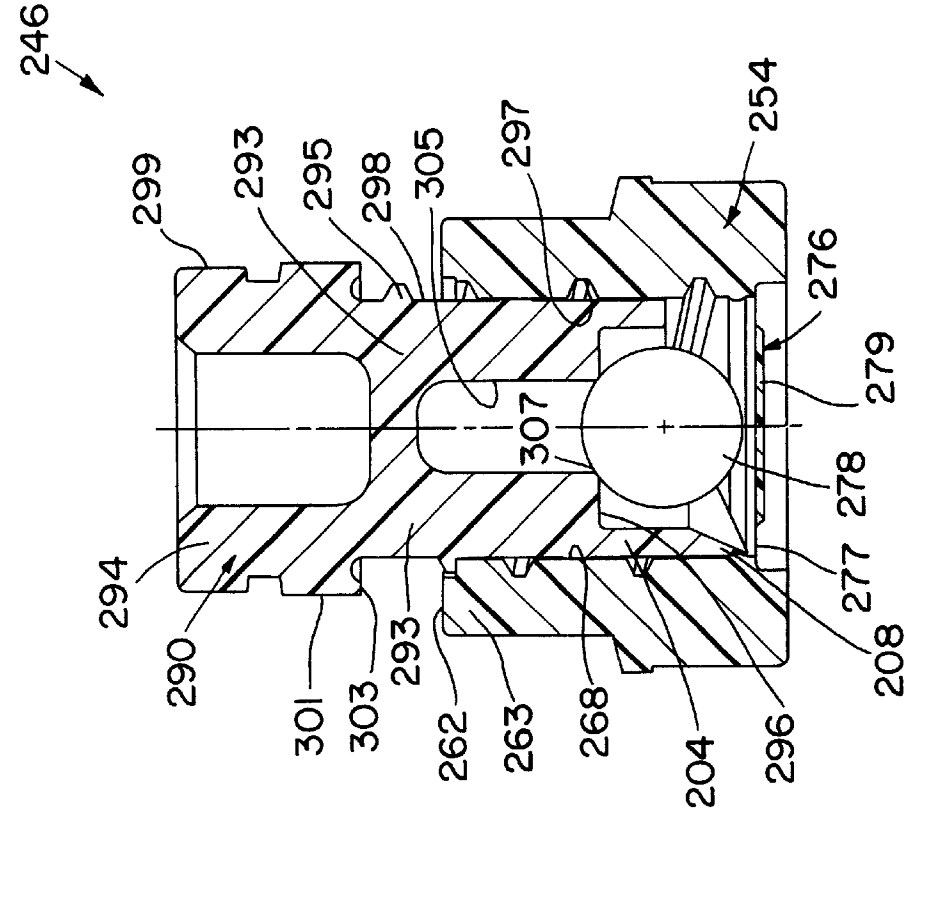
FIG. 6 is an enlarged, partial front sectional view of an alternate insert assembly embodying the present invention.

FIGS. 6 and 7 depict an alternate insert assembly, generally designated 246, which includes a plunger 290 with a plunger body portion 293 provided with external threads 295 that engage mating internal threads 297 formed in the base member 254 along the inner surface which defines a central passageway 268 thereof. In such a case, the plunger body portion 293 is urged against the membrane 27 by turning rather than pushing to partially sever the membrane 276 from base member 254.

The insert assembly 246 also differs in structure from the insert assembly 46 in that the outer surface 298 of plunger body portion 293 includes a knurled flange portion 29 which extends radially outwardly therefrom adjacent the proximal end 294 and allows the plunger body portion 293 to be easily grasped and turned.

A second flange portion 301 extends radially outwardly from the outer surface 298 in a parallel and spaced relationship relative to the knurled flange portion 299. The flange portion 301 defines a radial shoulder 303 which, as shown in FIG. 7, is adapted to abut against the shoulder 262 defined at the proximal end 263 of the base member 254 to limit the depth to which the plunger body portion 293 can be threaded into the passageway 268 defined in the base member 254.

The membrane 276 differs in structure from the membrane 176 associated with the insert assembly 46 in that the membrane 276 includes a peripheral portion 277 which is thinner than a central portion 279 thereof to further enhance the piercing of the membrane 276 by the tip or edge 208 of the piercing blade 204 which extends downwardly from the distal end face 296 of the plunger body portion 293.

The plunger 290 of the insert assembly 246 additionally differs in structure from the plunger 90 of the insert assembly 46 in that the plunger 290 includes an interior cavity 305 which terminates in an opening 307 in the distal end face 296 thereof. The opening 307 defines a cradle for the medicament tablet 278 housed in the pocket 270 in a manner similar to the cradle defined by the prongs 86 and 88 of the base member 54 of the insert assembly 46.

The other elements and features of the alternate insert assembly 246 are similar to the elements and features of the insert assembly 46.

Figure 8:
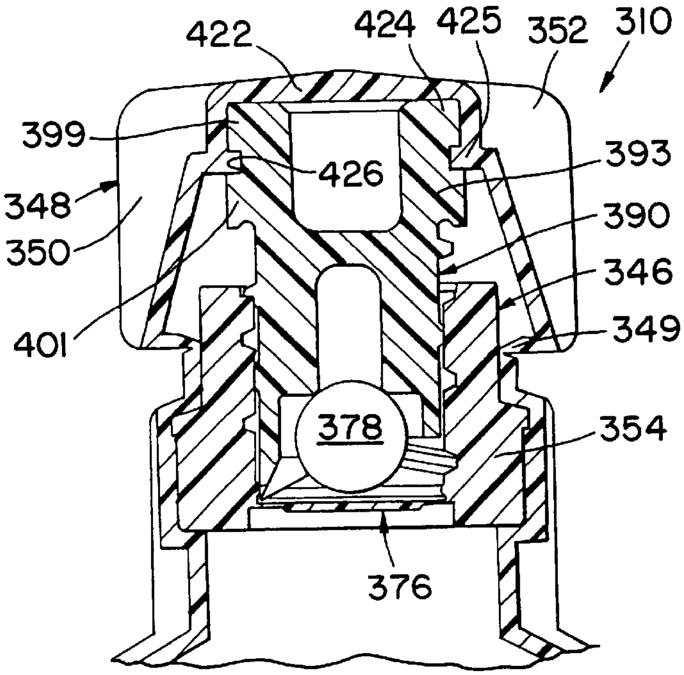
FIG. 8 is an enlarged, front sectional view of an alternate container embodying the present invention.

FIG. 8 depicts yet a further alternate container embodiment 310 including an insert assembly 346 which is similar in structure and function to the insert assembly 24 shown in FIGS. 6 and 7. The container embodiment 310 further includes a severable overcap 348 with grasping wings 350 and 351 unitary therewith. Overcap 348 is similar in structure to the overcap 48 shown in FIGS. 1 and 2, except that the thermoplastic material forming the overcap 348 also defines a container top portion 422 and stays together with body portion 393 of plunger 390 as body portion 393 is turned. In this particular embodiment, overcap 348 need not be removed in order to activate plunger 390. Flange portions 399 and 401 receive therebetween inwardly extending flange or ring 425 of the material that forms overcap 348.

The thermoplastic material forming the overcap 348 is brought into intimate and abutting relationship with the outer surface of the plunger 390 and the groove 426 defined therein by flange portions 399 and 401 during the molding of the container 10 and, more particularly, after the insertion and sealing of the insert assembly 346 as is known in the art and shown in U.S. Pat. No. 4,596,110 to Weiler and U.S. Pat. No. 4,707,966 to Weiler et al.

As a result, the overcap 348 is permanently secured to the plunger 390 such that, when the overcap 348 is twisted to break the unitary frangible web 349, the plunger 390 turns with the overcap 348. The subsequent turning of the overcap 348, in turn, causes the downwardly movement of the plunger 390 into piercing and severing contact with the membrane 376 in the same manner as described above with respect to the plunger embodiment 290 to dispense medicament 378.

What has thus been disclosed and described are containers including alternate insert assemblies which house and subsequently dispense a medicament into the container body thus eliminating the risk of contamination which can result when medicaments are handled or exposed to non-sterile environments prior to being mixed with a carrier liquid.

We claim:

1. A hermetically sealed container which comprises:

a container body portion which terminates at one end into a hollow neck portion that defines a socket;

a medicament bearing insert assembly sealingly received in said socket and including a base member permanently immobilized in said socket and defining a medicament pocket with a proximal aperture occluded by a rupturable membrane unitary with the base member; a solid medicament in said pocket; and a plunger engaged by said base member, movable in said pocket, and adapted to penetrate said membrane so as to dispense the medicament into the container through the proximal aperture in the base member but without fully severing the membrane from the base member;

a severable overcap unitary with the container and delineated from the neck portion by a frangible web.

2. The container in accordance with claim 1 wherein the plunger is provided with a tip for piercing and rupturing the membrane when the plunger is urged against the membrane.

3. The container in accordance with claim 1 wherein the container body portion terminates at an opposite end in a dispensing nozzle and the plunger is slidably movable into said pocket to pierce the membrane.

4. The container in accordance with claim 1 wherein the base member includes internal threads which engage external threads on the plunger and the plunger is threadedly movable into said pocket to sever a portion of the membrane about the periphery thereof.

5. The container in accordance with claim 4 wherein the overcap is made of thermoplastic material forming a ring which is brought into intimate and abutting relationship with a groove formed in the plunger so that the overcap is permanently secured to said plunger and said plunger is threadingly movable into said pocket in response to the turning of said overcap.

6. The container in accordance with claim 1 wherein the medicament is in the form of a capsule and the plunger includes a radial end face defining a cradle for the capsule.

7. The container in accordance with claim 6 wherein the cradle is defined by a pair of spaced-apart prongs extending outwardly from the radial end face of the plunger.

8. The container in accordance with claim 6 wherein the cradle is defined by a cavity in the plunger which terminates in an opening in the radial end face of the plunger.

* * * * *

UNITED STATES PATENT AND TRADEMARK OFFICE
CERTIFICATE OF CORRECTION

PATENT NO. : 6,387,073 B1
DATED : May 14, 2002
INVENTOR(S) : Gerhard H. Weiler et al.

It is certified that error appears in the above-identified patent and that said Letters Patent is hereby corrected as shown below:

Column 2,
Line 3, "invent ion," should be -- invention, --.
Line 49, "o" should be -- of --.
Line 51, "%ill" should be -- will --.
Line 66, "contain r" should be -- container --.

Column 3,
Line 11, "1" should be -- 12 --
Line 12, "general" should be -- generally --.
Line 13, "4A" should be -- 44 --.
Line 30, "t" should be -- to --.
Line 49, after "Medicament" delete "it".

Column 4,
Line 1, "o" should be -- of --.
Line 7 "c,n" should be -- can --.
Line 9, "defme" should be -- define --.
Line 11, after "76" insert a period (.).
Line 13, "5." should be -- 54. --.
Line 16, "o" should be -- of --.
Line 17, "d" should be -- and --.
Line 18, "t e" should be -- the --.
Line 22, "cuter" should be -- outer --.
Line 25, "flan ye" should be -- flange --.
Line 32, "e tends" should be -- extends --.
Line 35, "n" should be -- in --.
Line 66, "n" should be -- on --.

Column 5,
Line 25, "11." should be -- 13. --.
Line 39, "27" should be -- 276 --.
Line 44, "29" should be -- 299 --.

UNITED STATES PATENT AND TRADEMARK OFFICE

CERTIFICATE OF CORRECTION

PATENT NO. : 6,387,073 B1 
DATED : May 14, 2002
INVENTOR(S) : Gerhard H. Weiler et al.

It is certified that error appears in the above-identified patent and that said Letters Patent is hereby corrected as shown below:

Column 6,
Line 10, "24" should be -- 246 --.
Line 26, "10" should be -- 310 --.

Signed and Sealed this

Twenty-fifth Day of February, 2003

JAMES E. ROGAN
*Director of the United States Patent and Trademark Office*